(12) United States Patent
Taylor, Jr. et al.

(10) Patent No.: US 7,641,920 B2
(45) Date of Patent: Jan. 5, 2010

(54) METHODS AND COMPOSITIONS FOR MAINTAINING OR ENHANCING FEEDING CHARACTERISTICS IN POST-RECEIVING STRESSED ANIMALS

(75) Inventors: Don Taylor, Jr., St. John, KS (US); Larry C. McNeff, Anoka, MN (US)

(73) Assignee: SarTec Corporation, Anoka, MN (US)

( * ) Notice: Subject to any disclaimer, the term of this patent is extended or adjusted under 35 U.S.C. 154(b) by 378 days.

(21) Appl. No.: 11/241,237

(22) Filed: Sep. 30, 2005

(65) Prior Publication Data
US 2006/0073194 A1    Apr. 6, 2006

Related U.S. Application Data

(60) Provisional application No. 60/616,345, filed on Oct. 5, 2004.

(51) Int. Cl.
*A61K 36/00* (2006.01)
(52) U.S. Cl. ...................................... 424/725
(58) Field of Classification Search ........................ None
See application file for complete search history.

(56) References Cited

U.S. PATENT DOCUMENTS 5,139,779 A * 8/1992 McNeff ....................... 424/750

OTHER PUBLICATIONS

Hoffman et al. (Proceedings, Annual Meeting—American Society of Animal Science, Western Section (1977) vol. 28, pp. 204-207—abstract).*
DPI Distributors Processing Inc.,"Sevarin® with Sarsaponin: gets 'em from feedlot to market faster, more profitably". 1982.
Cheeke, P. R., "Actual and potential applications of Yucca schidigera and Quillaja saponaria saponins in human and animal nutrition", *Proc. Am. Soc. Anim. Sci.* 1999 (www.asas.org/symposia/proceedings/0909.pdf), (2000).
Dehority, Burk A., "Evaluation of Subsampling and Fixation Procedures Used for Counting Rumen Protozoa", *Appl. Environ. Microbiol.* 48(1), (Jul. 1984),182-185.
Dumitru, Razvan , "Targeting Methanopterin Biosynthesis To Inhibit Methanogenesis", *Appl. Environ. Microbiol.* 69(12), (Dec. 2003),7236-7241.
Fahmy, Wael G., "Effect of Defaunation and Amino Acid Supplementation on Growth and Amino Acid Balance in Sheep", (Aug. 5, 1998).
Francis, George, "The biological action of saponins in animal systems: a review." *Br. J. Nutr.* 88(6), (2002),587-605.
Goodall, S. R., "Rumensin with and without Sarsaponin for Finishing Feedlot Steers",*Col. Agr. Exp. Station* No. 700 , (1981).
Goodall, S. R., "Sarsaponin effects upon ruminal VFA concentrations and weight gain of feedlot cattle", *J. Anim. Sci.* 49 (1979),377-382.
Goodall, Richard S.; "Sarsaponin in Beef Cattle Rations", *Beef Nutrition Research*, (1978),9-10.
Goodall, S. R., "The Effect of Sarsaponin with and without Rumensin in High-Energy Diets", *Col. Agr. Exp. Station* No. 700, (1981).

Hristov, Alexander N., "Effect of Yucca schidigera on ruminal fermentation and nutrient digestion in heifers", *J. Anim Sci.* 77, (1999),2554-2563.
Klita, P. T., "Effects of alfalfa root saponins on digestive function in sheep", *J. Animal Sci.* 74, (1996), 1144-1156.
Koenig, K. M., "Effects of protozoa on bacterial nitrogen recycling in the rumen", *J. Anim Sci.* 78, (2000),2431-2445.
Lila, Z. A., "Effect of Sarsaponin on Ruminal Fermentation with Particular Reference to Methane Production in Vitro", *J. Dairy Sci.* 86, 2003,3330-3336.
Lu, C. D., "Alfalfa saponins affect site and extent of nutrient digestion in ruminants", *J. Nutr.* 117, (1987),919-927.
Mendoza, G. D., "Influence of ruminal protozoa on site and extent of starch digestion and ruminal fermentation", *J. Anim Sci.* 71, (1993),1572-1578.
Navas-Camacho, Alberto , "Effect of reducing the rumen ciliate protozoa population by feeding saponin-containing plants on rumen function of sheep fed on wheat straw", *Arch. Latinoam. Prod. Anim.* 5(*Supp. 1*), (1997),98-101.
Rush, Ivan , "Grain Tempering Agent (SarTemp) for Corn in Finishing Rations", *Beef Cattle Report*,(1993),63-64.
Towne, Gene, "Omasal Ciliated Protozoa in Cattle, Bison, and Sheep", *Appl. Environ. Microbiol.* 56(2), (Feb. 1990),409-412.
Valdez, F. R., "Effect of Steroidal Sapogenins on Ruminal Fermentation and on Production of Lactating Dairy Cows", *J. Dairy Sci.* 69, (1986),1568-1575.
Wallace, R. J., "Influence of Yucca Shidigera Extract on Ruminal Ammonia Concentrations and Ruminal Microorganisms", *Appl. Environ. Microbiol.* 60(6), (Jun. 1994),1762-1767.
Wang, Y., "Effects of Yucca Schidigera extract on fermentation and degradation of steroidal sponins in the rumen simulation technique (RUSITEC)", *Animal Feed Sci. Technol.* 74, (1998),143-153.
Wilson, R. C., "Effects of Yucca shidigera Extract and Soluble Protein on Performance of Cows and Concentrations of Urea Nitrogen in Plasma and Milk", *J. Dairy Sci.* 81, (1998),1022-1027.
Zinn, R. A., "Influence of tempering on the feeding value of rolled corn in finishing diets for feedlot cattle", *J. Anim Sci.* 76, (1998),2239-2246.
Choat et al., *Effect of Conventional* vs. *Restricted Adaptation to a High-Concentrate Diet on Performance and Carcass Characteristics of Feedlot Calves*, 2001 Animal Science Research Report.

* cited by examiner

*Primary Examiner*—Susan C Hoffman
(74) *Attorney, Agent, or Firm*—Pauly, DeVries Smith, & Deffner, L.L.C.

(57) ABSTRACT

The present invention relates to methods and compositions for maintaining or enhancing feeding characteristics of post-receiving stressed animals using a saponin composition. In an embodiment, the invention includes a method for increasing feed intake of an animal after a post-receiving stressful event comprising administering an effective amount of a composition comprising saponins to the animal. In an embodiment, the invention includes a method for increasing weight gain of an animal after a post-receiving stressful event comprising administering an effective amount of a composition comprising saponins to the animal.

17 Claims, 3 Drawing Sheets

METHODS AND COMPOSITIONS FOR MAINTAINING OR ENHANCING FEEDING CHARACTERISTICS IN POST-RECEIVING STRESSED ANIMALS

CROSS REFERENCE TO RELATED APPLICATION

This application claims the benefit of U.S. Provisional Patent Application Ser. No. 60/616,345, filed Oct. 5, 2004, which application is hereby incorporated by reference in its entirety.

FIELD OF THE INVENTION

The present invention relates to methods and compositions for maintaining or enhancing feeding characteristics of animals. More specifically, the present invention relates to methods and compositions for maintaining or enhancing feeding characteristics of animals that have been stressed post-receiving using a composition comprising saponins.

BACKGROUND OF THE INVENTION

Animals that have undergone a post-receiving stressful event such as handling, weighing, vaccination, implanting, ultrasonic back fat screening, pregnancy testing, etc., can exhibit reduced feed intake after the stressful event. The loss in feed intake has been observed to typically fall within a rage of 5-15% loss of feed intake on a dry matter basis. This reduced feed intake typically lasts for a period of 2-10 days. However, a significant percentage (30%) of these stressful events produce losses in feed intake that never fully recover.

Losses in feed intake can result in economic losses for cattle owners and feedlots alike. Specifically, a 10% drop in feed intake over a 5-day period can mean a loss of approximately 10 pounds of feed intake on a dry matter basis. When applied across the 25 million cattle produced in the US each year, a drop in 10 pounds of feed intake translates to a loss of approximately 25-50 million pounds of beef and 250 million pounds of feed not consumed for a total economic impact of 35-60 million per stress event (assuming a fat cattle price of $0.80/pound, a ration cost of $0.07/pound and a feed conversion rate of 5-10 pounds of feed per pound of gain). The economic impact is even greater when considering the significant percentage of animals that never recover from a stressful event for which feed intake is depressed for the remainder of their lives. These steers that never fully recover may have decreased average daily gain numbers on the order of 0.4 pounds per day. Thus, for example, over an 80-day period this decrease can result in 32 pounds less gain.

Therefore, a need exists for methods and compositions for maintaining or enhancing feeding characteristics of animals.

SUMMARY OF THE INVENTION

The present invention relates to methods and compositions for maintaining or enhancing feeding characteristics of post-receiving stressed animals using a composition comprising saponins. In an embodiment, the invention includes a method for increasing feed intake of an animal after a post-receiving stressful event comprising administering an effective amount of a composition comprising saponins to the animal. In an embodiment, the invention includes a method for increasing weight gain of an animal after a post-receiving stressful event comprising administering an effective amount of a composition comprising saponins to the animal.

DETAILED DESCRIPTION OF THE INVENTION

In the course of agricultural production, animals undergo a variety of post-receiving stressful events including handling, weighing, vaccination, implanting, ultrasonic back fat screening, pregnancy testing, etc. For example, stress associated with re-implanting has to do with handling of the animal and physically injecting it with an implanted device. It has been observed that animals frequently exhibit reduced feed intake after the post-receiving stressful event. As used herein, the term "post-receiving" refers to the time period after arrival at a feed yard.

It has been surprisingly discovered that administration of a saponin composition can counteract the loss in feed intake that is observed after a stressful event. In an embodiment, the invention includes a method for increasing feed intake of an animal after a post-receiving stressful event comprising administering an effective amount of a saponin composition to the animal. In an embodiment, the invention includes a method for increasing weight gain of an animal after a post-receiving stressful event comprising administering an effective amount of a saponin composition to the animal.

Saponins

Saponins are natural plant surfactants that occur in over 500 different plant species belonging to some 80 different families. Saponins are generally recognized by their strong foaming action when placed in water, which has made them especially useful in the manufacture of foods, beverages, shampoos, wetting agents and pharmaceuticals.

Figure 1:
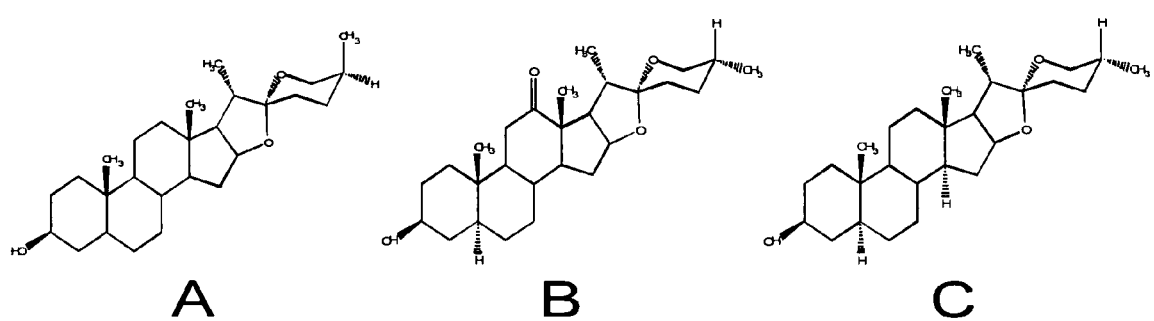
FIG. 1 shows the chemical structures of the three sapogenins present in *Yucca schidigera*.
Figure 2:
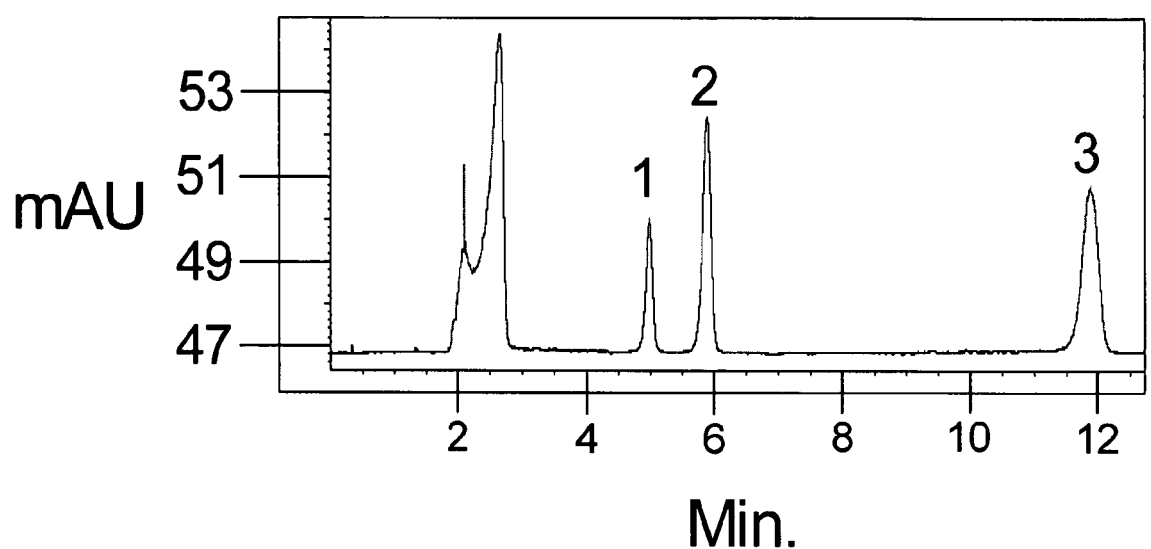
FIG. 2 shows the separation of (1) sarsasapogenin, (2) tigogenin, and (3) hecogenin by normal-phase HPLC.

Saponins are classified as surfactants because they have both lipophilic and hydrophilic "regions". Thus, the surfactant activity of saponins is a result of both fat-soluble and water-soluble moieties in the same molecule. The lipophilic region may be a steroid, triterpene or alkaloid, and is termed a sapogenin. The hydrophilic "region" contains one or more water-soluble carbohydrate side chains. Yucca derived saponins generally have steroidal sapogenins. Referring now to FIG. 1, the chemical structures of the three sapogenins present in *Yucca schidigera* are shown: A) sarsasapogenin, B) hecogenin, and C) tigogenin. Sarsasapogenin is the major sapogenin found in the *Yucca schidigera* plant. Saponins have an antiprotozoal activity attributed to the saponin's ability to interact with cholesterol in protozoal cell membranes and cause cell lysis. Referring now to FIG. 2, the separation of three sapogenins by normal phase HPLC is shown. Specifically, FIG. 2 shows separation of (1) sarsasapogenin, (2) tigogenin, and (3) hecogenin by normal-phase HPLC.

The structural complexity of saponins is derived largely from the carbohydrate portion of the molecule due to the many different types of possible side chain carbohydrates, such as glucose, xylose, galactose, pentose or methylpentose, which may have different connectivity and/or anomeric configuration.

Saponin Compositions

Saponins useful in the present invention can be extracted from plants of the family: Amaryllidaccae, genus: *Agave*, which grows extensively in the southwestern United States and in Mexico. Saponins useful in the present invention may also be extracted from plants of the family: Lillaecae, genus: *Yucca*, such as *Yucca schidigera*. Saponins may also be obtained from extracts of soybeans, fenugreek, ginseng, peas, tea, yams, sugar beets, alfalfa, asparagus, aloe, vanilla, zhimu (or zhi-mu, Anemarrhena root), *Sapindus saponaria*, as well as from *Quillaja saponaria* bark. Saponins may be extracted from plant materials in accordance with techniques well known by those of skill in the art.

The Yucca plant is a wide-ranging genus, which is part of the Century plant family, Aguavacea. Taxonomically there are 30 species within the *Yucca* genus, *Schidigera* being one. Yucca plants thrive mainly in semi-arid climates such as are found in India, Angola, Italy, Southwest U.S., and Mexico to name a few. Yucca extract has been historically used among the Native American population in Mexico and the United States for medicinal purposes. It is approved by the U.S. Food and Drug Administration (FDA) as a natural food additive under 21 C.F.R. § 172.510. It has been used as a dietary supplement without evidence of toxicity.

Yucca extracts are approved for use in animal feeds as listed in the official publication of the Association of American Feed Control Officials, Inc. as a flavoring agent (IFN 8-19-700, reg 172.510). Yucca extracts have been fed to livestock in low doses for many years. However, embodiments of the current invention involve the oral administration of a higher dosage of a saponin liquid or dry supplement to an animal in order to counteract the loss in feed intake that is observed after a stressful event.

In general, the extracts are considered safe for use in animal feeds and for human consumption. The EPA has ruled that Yucca extract is exempt from the requirement of a tolerance. In regards to toxicology, an acute oral gavage toxicity study performed on Sprague-Dawley derived rats was performed using a 70% yucca extract syrup. The LD50 for males was found to be greater than 5,000 mg/kg, and for females it was calculated to be greater than 500 mg/kg.

The typical saponin content that naturally occurs in yucca plants is from 0.1-2% saponins by weight. Yucca extracts can be derived by extracting yucca powder with an aqueous solution that may or may not contain some fraction of organic solvent such as methanol, ethanol, propanol, butanol, or the like. Commercially available Yucca extracts can have a total solids content usually in the range from 5-50%. The saponin content of a typical 50 brix (50% solids by weight) yucca extract is usually in the range of about 1-2% saponins by weight as measured by HPLC analysis. Another method of measuring total saponin content is the extraction of all soluble components into a butanol extract followed by gravimetric analysis of the compounds dissolved in the butanol fraction. Measuring saponin content by the butanol extract method typically results in higher numbers than the more advanced HPLC method. Accordingly, the typical 50 brix (50% solids by weight) yucca extract is usually in the range of about 5-20.0% saponins content by weight as measured by the butanol extract method.

In an embodiment, the saponin composition used in accordance with the invention comprises at least 0.1% by weight saponins as measured by HPLC. In an embodiment, the saponin composition used in accordance with the invention comprises at least 0.5% by weight saponins as measured by HPLC. In a particular embodiment, the saponin composition used in accordance with the invention comprises at least 1.0% by weight saponins as measured by HPLC. It is believed that the effects of the composition are related to the total amount of saponins present. Thus, one of skill in the art will appreciate that if a certain amount of saponins is desired it can be achieved either through varying the volume of a certain concentration composition administered, varying the concentration of a certain volume of a composition, or both.

Exemplary liquid solutions containing saponins are available commercially and sold under the trademarks SARTEMP®, SARSTART®, SARSTART® PRO, and SARSTART® PLUS by SarTec Corporation of Anoka, Minn. These solutions are prepared by blending an aqueous extract of the plants of the family: Lillaecae, genus: Yucca, or other appropriate Yucca plants with antifreeze agents such as calcium chloride, propylene glycol, and the like, to depress the freezing point to approximately −30° F. Saponin compositions may also comprise a variety of other components. By way of example, SARSTART® PLUS can contain the following ingredients: water, propylene glycol, *Yucca schidigera* extract, vitamin E (as di-alpha-tocopheryl acetate), vitamin A propionate, vitamin A palmitate, vitamin B1, vitamin B2, vitamin B6, vitamin B12, D-Activated animal sterol (source of Vitamin D3), naturally occurring organisms, dried egg solids, dried casein, and dried whey. The physical and chemical characteristics of SARSTART® PLUS are as follows: Boiling Point: 240° F.; Specific Gravity: 1; Melting Point: −20 F; Solubility in Water: Miscible; Appearance and Odor: Dark brown liquid with a mild odor and a slightly acid taste. Saponin containing compositions can also be formulated as dry powder. Such dry formulations are available commercially (SARSTART® D, SARSTART® DSC, SarTec Corporation, Anoka, Minn.). Dry powder formulations of saponin compositions may be added to the feed ration via a micro-ingredient machine or added to a feed mix truck and mixed thoroughly to assure even distribution in the feed.

Saponin compositions can be administered through many different means known to those of skill in the art. For example, liquid saponin compositions can be administered orally through the use of a drench gun. A saponin composition may also be mixed with feed, pressed into pill form, etc.

Post-Receiving Stressful Events:

As stated above, animals may experience many stressful events after arrival at a feed yard including handling, weighing, vaccination, implanting, re-implanting, ultrasonic back fat screening, pregnancy testing, weather-related stress, etc. For example, cattle may be implanted with devices that slowly release hormones in order to enhance growth. Frequently, these cattle must be re-implanted at various time intervals because the devices will eventually stop releasing hormones. Re-implanting can be a stressful event for an animal and can result in decreased feed intake.

Animals may also experience stresses during the shipping and receiving process. For example, during shipping the animals are not given feed or water. However, shipping and receiving stresses can be distinguished from post-receiving stresses because post-receiving stresses generally do not involve withdrawal of feed or water over an extended period of time. For example, post-receiving stresses generally do not involve withdrawal of feed or water for a period of time greater than about four hours. While not intending to be bound by theory, it is believed that this distinction is significant because animals that have gone without feed or water for an extended period develop a higher level of ruminal protozoa. The protozoa produce L-pipecolic acid, which has been linked to a reduction in appetite and alertness. As saponins have anti-protozoan activity, they can be used to counteract the reduction in appetite caused during shipping and receiving.

In contrast, it is believed that the loss in appetite resulting from post-receiving stresses, are largely a result of simply physically disturbing the animals, such as occurs when re-implanting them. To wit it has been shown that non-stressed cattle are more productive and therefore more profitable than animals that are stressed. See Feedlot, (September/October 2005), p. 10-11. In one study, non-stressed cattle showed an 11 pound greater weight gain, on average, than comparable stressed cattle over the first 50 days after weaning. However, as the reduction in appetite resulting from post-receiving stresses does not appear to be primarily linked to increased protozoal populations, it was unexpected that saponins could, in effect, act as a stress reliever and at least partially mitigate the loss in feed intake that typically results from a post-receiving stress event.

Dosing of Saponin Compositions:

Saponin compositions in accordance with the invention may be in liquid or dry forms. By way of example, a yucca containing plant extract can be dried into a powder form. In this form, the yucca containing composition may be administered to an animal as a pill or bolus, gel, paste, or mixed in with other components such as a feed ration. A saponin composition can also be in a solution with an amount of a carrier liquid such as water. In this form, the saponin composition can be administered to an animal as a liquid drench.

A saponin composition can be administered to an animal as a single dose. Saponin compositions can also be administered as a plurality of doses. For example, as an initiation dose, at or around the time of a stressing causing event, followed by a smaller daily dose thereafter. The dose(s) can be administered as a bolus or mixed in with daily feed. A smaller daily dose can be administered after the initiation dose and throughout the finishing phase. In an embodiment, a smaller daily dose is continued for at least 28 days. In an embodiment, a smaller daily dose is continued for at least 60 days.

In an embodiment of the invention, the initiation dose, is larger than each of the smaller daily doses, or maintenance doses. In an embodiment the initiation dose is at least 3 times larger (3 times larger amount of saponins) than the daily dose. In an embodiment, the initiation dose is at least 5 times larger than the daily dose. In a particular embodiment, the initiation dose is at least 15 times larger than the daily dose.

Administration of the saponin composition can conducted at, or around, the time of stress causing event. For example, in an embodiment, the dose, or initiation dose, is administered within five days before or after the time of re-implanting the cattle at the feedlot. In some applications, the dose, or initiation dose, is administered close to the time of the stress-causing event. In an embodiment, the dose, or initiation dose, is administered within 48 hours before or after the time of the post-receiving stress causing event. The dose, or initiation dose may also be administered within 24 hours before or after the time of the post-receiving stress causing event. In a specific embodiment, the dose, or initiation dose, is administered the same day as the post-receiving stress causing event.

The present invention may be better understood with reference to the following examples. These examples are intended to be representative of specific embodiments of the invention, and are not intended as limiting the scope of the invention.

EXAMPLES

Example 1

Effect of Saponin Composition at Re-implant Time

As discussed above, cattle may be implanted with devices, such as a pellet, that slowly release hormones in order to enhance growth. Frequently, these cattle must be re-implanted at various time intervals because the devices will eventually stop releasing hormones. For example, in the finishing phase for beef cattle, re-implant time can occur 60 days after the cattle are received at a feed yard. Re-implanting is a stressful event for the cattle. Consequently, feed intake can be adversely affected after re-implanting.

Five pens of cattle were selected for testing the effects of administering a saponin composition at re-implant time. The five pens of cattle had all previously been treated with one 50 mL dose of a saponin composition containing about 0.1 wt. % saponins (SARSTART® LSC, SarTec, Anoka, Minn.) on the day they first arrived at the feed yard (day 0). Of the five pens of cattle, three pens were selected for treatment with a saponin composition at the time of re-implant (day 60, meaning 60 days after arrival at the feed yard) (Pen 1, Pen 2, and Pen 3. The remaining two pens of cattle were selected to serve as an experimental control (Pen 4 and Pen 5), receiving no saponin composition drench at the time of re-implant (day 60).

Figure 3:
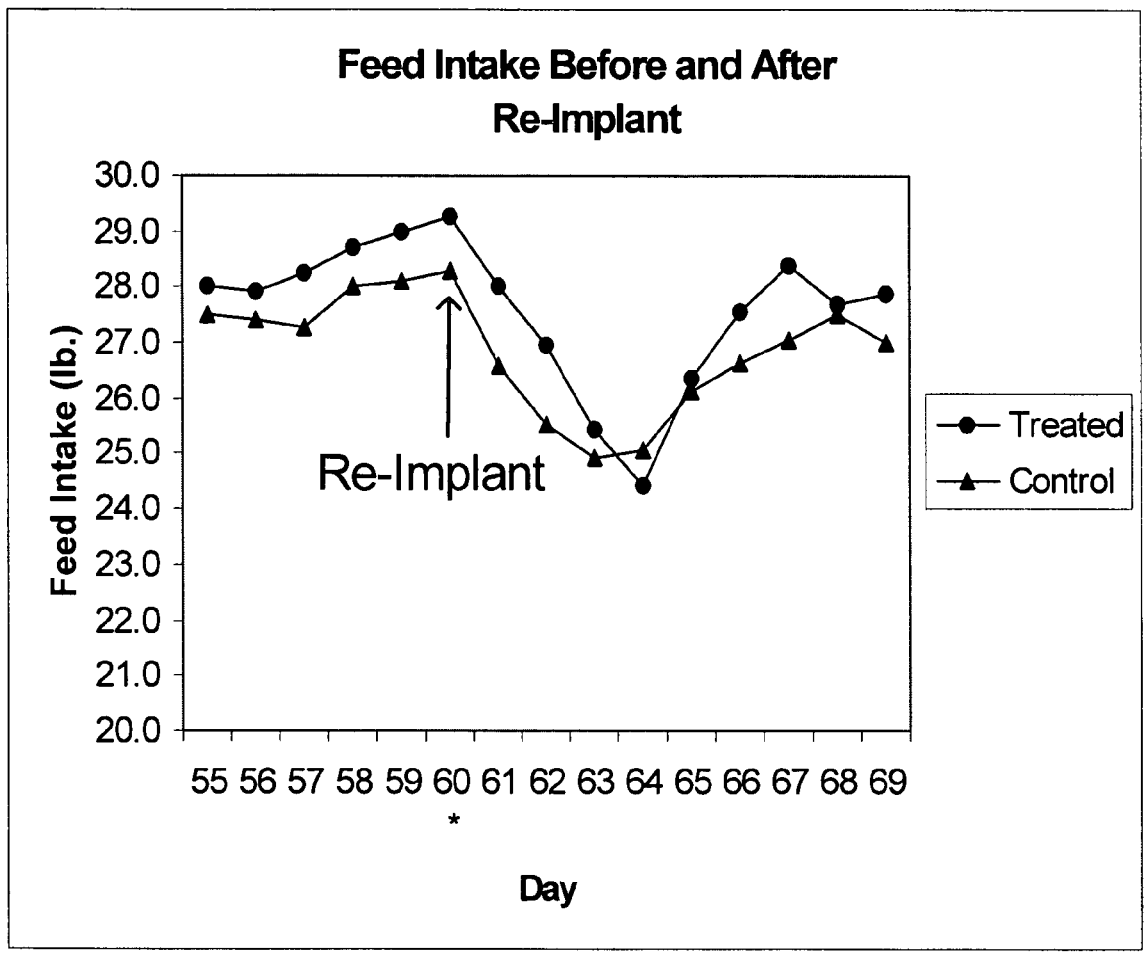
FIG. 3 shows the effects of treatment with a saponin composition on feed intake in cattle, around re-implant time.

Both the treatment groups and the control groups were kept in accordance with standard feed yard operating procedures. Both the treatment groups and the control groups were given ad libitum access to food and water. Consumption (feed intake) of feed in pounds was monitored daily. Cattle from all groups were re-implanted on day 60. The treatment groups were given a 50 mL bolus dose (per head) of a Yucca extract saponin composition comprising about 0.1 wt. % saponins (SARSTART®, SarTec, Anoka, Minn.) on day 60. The average pounds of feed intake per steer for each pen are shown in Table 1 below and in FIG. 3.

TABLE 1

| Day | Treated (intake in lbs) | | | | Control (intake in lbs) | | |
| --- | --- | --- | --- | --- | --- | --- | --- |
| | Pen 1 | Pen 2 | Pen 3 | Avg. | Pen 4 | Pen 5 | Avg. |
| 55 | 27.2 | 29.8 | 27.0 | 28.0 | 27.8 | 27.2 | 27.5 |
| 56 | 26.9 | 28.4 | 28.5 | 27.9 | 27.3 | 27.5 | 27.4 |
| 57 | 27.0 | 28.1 | 29.6 | 28.2 | 27.1 | 27.5 | 27.3 |
| 58 | 27.9 | 28.8 | 29.4 | 28.7 | 28.7 | 27.3 | 28.0 |
| 59 | 27.9 | 29.0 | 30.0 | 29.0 | 29.0 | 27.2 | 28.1 |
| 60 * | 28.2 | 29.5 | 30.1 | 29.3 | 29.0 | 27.6 | 28.3 |
| 61 | 27.9 | 27.9 | 28.2 | 28.0 | 27.1 | 26.1 | 26.6 |
| 62 | 27.2 | 27.6 | 26.1 | 27.0 | 26.0 | 25.1 | 25.6 |
| 63 | 26.1 | 26.0 | 24.2 | 25.4 | 25.9 | 24.0 | 25.0 |
| 64 | 23.8 | 26.2 | 23.3 | 24.4 | 25.9 | 24.2 | 25.1 |
| 65 | 26.2 | 27.8 | 25.1 | 26.4 | 27.1 | 25.2 | 26.2 |
| 66 | 27.7 | 29.0 | 26.0 | 27.6 | 27.5 | 25.8 | 26.7 |
| 67 | 27.9 | 29.0 | 28.2 | 28.4 | 27.8 | 26.3 | 27.1 |
| 68 | 27.7 | 28.4 | 27.0 | 27.7 | 28.3 | 26.7 | 27.5 |
| 69 | 27.7 | 28.9 | 27.0 | 27.9 | 27.9 | 26.1 | 27.0 |

* = day of re-implant

The data show that cattle treated with an effective dose of a saponin composition regain normal feed intake more quickly after a post-receiving stressful event, such as re-implanting, than untreated cattle do.

Unless indicated to the contrary, all references to amounts of saponins contained herein are as measured by HPLC analysis. The invention has been described with reference to various specific and preferred embodiments and techniques. However, it should be understood that many variations and modifications may be made while remaining within the spirit and scope of the invention.

We claim:

1. A method for increasing feed intake of an animal after a post-receiving stressful event comprising:
    administering an effective amount of a composition comprising saponins to the animal within five days before or after re-implanting of the animal, the composition comprising an extract of *Yucca schidigera*.

2. The method of claim 1, wherein the amount of saponins administered is greater than about 0.05 grams.

3. The method of claim 1, wherein the amount of saponins administered is greater than about 0.1 grams.

4. The method of claim 1, wherein the amount of saponins administered is greater than about 0.5 grams.

5. The method of claim 1, wherein the administration of the composition is begun within 24 hours before or after the post-receiving stressful event.

6. The method of claim 1, the animal comprising a ruminant.

7. The method of claim 6, the animal comprising *Bos taurus*.

8. The method of claim 1, the saponins comprising sarsasaponins.

9. The method of claim 1, comprising administering the composition as a bolus dose.

10. The method of claim 1, wherein administering the composition comprises:
    administering an initiation dose of a first saponin composition, and
    administering a plurality of maintenance doses of a second saponin composition.

11. The method of claim 10, the initiation dose comprising a larger amount of saponins than each of the maintenance doses individually.

12. The method of claim 10, wherein the first saponin composition and the second saponin composition are the same.

13. The method of claim 10, wherein administering an initiation dose is performed on a single day.

14. The method of claim 10, wherein administering a plurality of maintenance doses is performed over a plurality of days.

15. A method for increasing weight gain of an animal after a post-receiving stressful event comprising:
    administering an effective amount of a composition comprising saponins to the animal, wherein the composition is administered within five days before or after the post-receiving stressful event, the post-receiving stressful event comprising re-implanting of the animal, the composition comprising an extract of *Yucca schidigera*.

16. The method of claim 15, comprising administering the composition as a bolus dose.

17. A method for increasing feed intake of an animal after a post-receiving stressful event comprising:
    administering an effective amount of a composition comprising saponins to the animal within five days before or after re-implanting of the animal, wherein the administration of the composition is begun within 24 hours before or after the post-receiving stressful event, the composition comprising an extract of at least one of *yucca* or alfalfa.

* * * * *

UNITED STATES PATENT AND TRADEMARK OFFICE
CERTIFICATE OF CORRECTION

PATENT NO. : 7,641,920 B2
APPLICATION NO. : 11/241237
DATED : January 5, 2010
INVENTOR(S) : Taylor, Jr. et al.

Page 1 of 1

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 840 days.

Signed and Sealed this

Sixteenth Day of November, 2010

David J. Kappos
*Director of the United States Patent and Trademark Office*